United States Patent [19]

Nakamura et al.

[11] Patent Number: 4,954,341
[45] Date of Patent: Sep. 4, 1990

[54] HAIR COSMETIC COMPOSITION

[75] Inventors: Sigemi Nakamura, Chiba; Hideo Kurokawa, Machida; Jouji Mitamura, Tokyo, all of Japan

[73] Assignee: Lion Corporation, Tokyo, Japan

[21] Appl. No.: 220,957

[22] Filed: Jun. 21, 1988

Related U.S. Application Data

[63] Continuation-in-part of Ser. No. 938,491, Dec. 5, 1986, abandoned.

[30] Foreign Application Priority Data

Dec. 10, 1985 [JP] Japan ................. 60-278813

[51] Int. Cl.$^5$ .............................................. A61K 7/00
[52] U.S. Cl. ...................... 424/70; 514/788; 514/772
[58] Field of Search .................. 424/70; 514/772, 788

[56] References Cited

U.S. PATENT DOCUMENTS

| | | | |
|---|---|---|---|
| 3,577,528 | 5/1971 | McDonough et al. | 424/70 |
| 4,452,732 | 6/1984 | Bolich, Jr. | 424/70 |

FOREIGN PATENT DOCUMENTS

| | | | |
|---|---|---|---|
| 52-122638 | 10/1977 | Japan . | |
| 55-4347 | 1/1980 | Japan . | |
| 55-27134 | 2/1980 | Japan . | |
| 55-75478 | 6/1980 | Japan . | |
| 120507 | 9/1980 | Japan | 424/70 |
| 56-77217 | 6/1981 | Japan . | |
| 56-77218 | 6/1981 | Japan . | |
| 56-110608 | 9/1981 | Japan . | |
| 57-56411 | 4/1982 | Japan . | |
| 56411 | 4/1982 | Japan | 424/70 |
| 57-112318 | 7/1982 | Japan . | |
| 59-70606 | 4/1984 | Japan . | |
| 59-70607 | 4/1984 | Japan . | |
| 222407 | 10/1985 | Japan | 424/70 |
| 12608 | 1/1986 | Japan | 424/70 |
| 15817 | 1/1986 | Japan | 424/70 |
| 61913 | 3/1987 | Japan . | |
| 138415 | 6/1987 | Japan . | |

*Primary Examiner*—Ellis P. Robinson
*Assistant Examiner*—Susan S. Rucker

*Attorney, Agent, or Firm*—Armstrong, Nikaido, Marmelstein, Kubovcik & Murray

[57] ABSTRACT

A hair cosmetic composition comprising:
(A) 0.05% to 10% by weight of at least one quaternary ammonium salt having the formula:

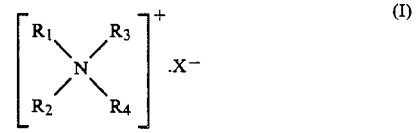

wherein $R_1$ is an alkenyl having 14 to 20 carbon atoms, $R_2$ is an alkyl or alkenyl having 14 to 20 carbon atoms, $R_3$ and $R_4$ are independently methyl, ethyl, a polyoxyethylene having an average polymerization degree of 1 to 5, or a polyoxypropylene having an average polymerization degree of 1 to 5, and $X^-$ is an anion, and having an iodine value of 35 to 100; and
(B) 0.05% to 10% by weight of a phosphate having the formula:

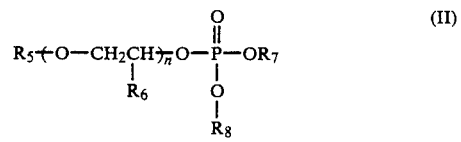

wherein $R_5$ is a linear alkyl having 1 to 22 carbon atoms, a hydroxyalkyl having 1 to 22 carbon atoms, an alkenyl having 2 to 22 carbon atoms, an alkylphenyl having 7 to 22 carbon atoms, or glyceryl, $R_6$ is hydrogen or methyl, $R_7$ is hydrogen, an alkali metal, a $C_1$–$C_{20}$ alkyl-substituted ammonium, or a $C_1$–$C_{20}$ hydroxyalkyl-substituted ammonium, $R_8$ is a group having the formula

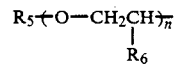

or $R_7$, n is an integer of 0 to 100, and $R_5$ and $R_6$ are the same as defined above.

5 Claims, No Drawings

HAIR COSMETIC COMPOSITION

CROSS REFERENCE TO RELATED APPLICATION

This application is a continuation-in-part of Ser. No. 938,491, filed Dec. 5, 1986 now abandoned.

BACKGROUND OF THE INVENTION

1. Field of the Invention

The present invention relates to a hair cosmetic composition capable of providing an excellent finish and setting effects to the hair.

2. Description of the Related Art

Conventional hair cosmetic compositions have primarily included quaternary ammonium salts, as exemplified by disteryl dimethyl ammonium chloride or stearyl trimethyl ammonium chloride, as main ingredients. Such hair cosmetic compositions are attracted to the anionic parts of the hair to reduce the generation of static electricity, thus suppressing hair disorder when combing and improving the comb-through characteristic.

Recent trends in setting, however, have been toward a more natural look and for a greater degree of freedom in individual hair styles. Hair cosmetic compositions based on conventional quaternary ammonium salts impart greater flexibility to the hair, but take away "body", and thus the hair becomes limp. As a result, a problem arises in that subsequent hair treatment, i.e., setting and waving, becomes difficult.

SUMMARY OF THE INVENTION

Accordingly, the objects of the present invention are to eliminate the above-mentioned problems and to provide a hair cosmetic composition which improves the settability and poor "body" of hair treated with conventional hair cosmetic compositions and has excellent comb-through, smoothness, softness, and antistatic characteristics.

Other objects and advantages of the present invention will be apparent from the description set forth hereinbelow.

In accordance with the present invention, there is provided a hair cosmetic composition comprising:

(A) 0.05% to 10% by weight of at least one quaternary ammonium salt having the formula:

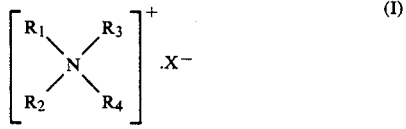

wherein $R_1$ is an alkenyl having 14 to 20 carbon atoms, $R_2$ is an alkyl or alkenyl having 14 to 20 carbon atoms, $R_3$ and $R_4$ are independently methyl, ethyl, a polyoxyethylene having an average polymerization degree of 1 to 5, or a polyoxypropylene having an average polymerization degree of 1 to 5, and $X^-$ is an anion, and having an iodine value of 35 to 100; and (B) 0.05% to 10% by weight of a phosphate having the formula:

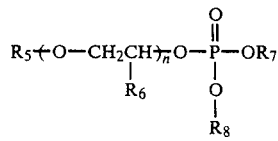

wherein $R_5$ is a linear alkyl having 1 to 22 carbon atoms, a hydroxyalkyl having 1 to 22 carbon atoms, an alkenyl having 2 to 22 carbon atoms, an alkylphenyl having 7 to 22 carbon atoms, or glyceryl, $R_6$ is hydrogen or methyl, $R_7$ is hydrogen, an alkali metal, a $C_1$-$C_{20}$ alkyl-substituted ammonium, or a $C_1$-$C_{20}$ hydroxyalkyl-substituted ammonium, $R_8$ is a group having the formula

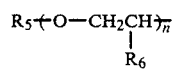

or $R_7$, n is an integer of 0 to 100, and $R_5$ and $R_6$ are the same as defined above.

DESCRIPTION OF THE PREFERRED EMBODIMENTS

According to the present invention, hair cosmetic compositions having excellent setting properties, comb-through characteristics, static friction coefficients, and antistatic properties can be obtained by the synergetical action of the combined use of the above-mentioned quaternary ammonium salts and the phosphate.

The quaternary ammonium salts usable as the first essential component (A) in the present invention are di-long chain and di-short chain type quaternary ammonium salts having the general formula (I):

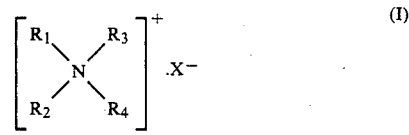

wherein $R_1$, $R_2$, $R_3$, $R_4$, and X are the same as defined above. These compounds can be used alone or in any mixture thereof.

The group $R_1$ in the formula (I) is an alkenyl and $R_2$ in the formula (I) is an alkyl or alkenyl. The carbon atom numbers of $R_1$ and $R_2$ are independently 14 to 20, preferably 16 to 18 and may be those having distributions within these ranges. When the carbon numbers of $R_1$ and/or $R_2$ are less than 14, the hydrophilicity is increased and the adsorpability is decreased and, therefore, the advantageous effects of the present invention are unpreferably impaired due to the desorption caused by, for example, rinsing. Contrary to this, when the carbon atom numbers of $R_1$ and/or $R_2$ are more than 20, the surface activity is lost and, therefore, the advantageous effects of the present invention disappear because the component (A) is not adsorbed on the hair. Furthermore, $R_3$ and $R_4$ are independently selected from the group consisting of methyl, ethyl, polyoxyethylene having an average polymerization degree of 1 to 5, and polyoxypropylene having an average polymerization degree of 1 to 5. Of this group, the use of methyl as $R_3$ and $R_4$ is preferable. The $X^-$ in the formula (I) may be any anion but preferably represents a halogen anion or $R_9 SO_4^-$, wherein $R_9$ is an alkyl having 1 to 3 carbon atoms. As the halogen anion, such as chlorine, bromine, or iodine anions, preferably chlorine anion is used.

The quaternary ammonium salts usable in the present invention are those having an iodine value of 35 to 100, preferably 40 to 90. When the iodine value is less than 35, the hydrophobicity is increased and, therefore, the finish becomes sticky. Contrary to this, when the iodine value is more than 100, the hydrophilicity is increased and the adsorpability is decreased and, therefore, the desired objects of the present invention cannot be attained. Note, quaternary ammonium salts not having the iodine value of 35 to 100 can be used in the present detergent composition so long as the overall iodine value of the mixed quaternary ammonium salts is within the above-mentioned range.

The quaternary ammonium salts having the formula (I) can be prepared, as a starting material, from unsaturated higher fatty acids such as oleic acid, linolic acid, and linoleic acid; or natural fatty acids such as palm oil fatty acid, soybean oil fatty acid, safflower oil fatty acid, tall oil fatty acid, and colza oil fatty acid; or the mixture thereof. Of these acids, the use of oliec acid, a mixture of oleic acid with tallow fatty acid, or palm oil fatty acid is preferable. When the quaternary ammonium salts usable in the present invention are synthesized from the above-mentioned starting material, the conventional process steps (e.g., fatty acid→nitrilization→secondary long-chain fatty amine formation→short-chain alkylization→quaternarization) can be utilized. During the synthesis, the reaction conditions can be selected so that the unsaturated bond % of the starting fatty acids is not decreased and the desired high iodine value can be finally retained.

The quaternary ammonium salts having the formula (I) are formulated into the present hair cosmetic compositions in an amount of 0.05% to 10% by weight, preferably 0.5% to 2.5% by weight, based on the weight of the composition. When the amount of the quaternary ammonium salt is less than 0.05% by weight, the desired effects of the present invention are not attained. Contrary to this, the formulation of the quaternary ammonium salt of more than 10% by weight into the composition is economically disadvantageous and results in a thick finish.

The phosphates usable as the second essential component (B) in the present hair cosmetic composition are those having the formula (II):

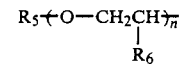

wherein $R_5$, $R_6$, $R_7$, $R_8$, and n are the same as defined above. These phosphates may be used alone or in any mixture thereof.

In the formula (II), $R_5$ is a linear alkyl having 1 to 22 carbon atoms, preferably 4 to 18, a hydroxyalkyl having 1 to 22 carbon atoms, preferably 4 to 18 carbon atoms, an alkenyl having 2 to 22 carbon atoms, preferably 4 to 18 carbon atoms, an alkylphenyl having 7 to 22 carbon atoms, or glyceryl, $R_6$ is hydrogen or methyl, $R_7$ is hydrogen, an alkali metal (e.g., sodium, potassium), a $C_1$–$C_{20}$ alkyl-substituted ammonium, or a $C_1$–$C_{20}$ hydroxyalkyl-substituted ammonium (e.g., triethanol amine, amino methyl propanol, triisopropanol amine), $R_8$ is a group having the formula

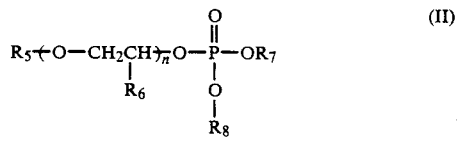

or $R_7$, n is an integer of 0 to 100, preferably 1 to 80, and $R_5$ and $R_6$ are the same as defined above.

The phosphates having the general formula (II) are formulated into the present hair cosmetic compositions in an amount of 0.05% to 10% by weight, preferably, 0.5 to 2.5% by weight, based on the weight of the composition. When the amount of the phosphate is less than 0.05% by weight, the desired effects of the present invention are not attained Contrary to this, the formulation of more than 10% by weight of the phosphate into the composition is economically disadvantageous and results in a thick finish.

In the hair cosmetic composition according to the present invention, the weight ratio of the quaternary ammonium salt (A) to phosphate (B) (i.e., A/B) is preferably 1/10 to 10/1, more preferably ½ to 1/5. The total amount of the components (A) and (B), formulated into the hair cosmetic composition is preferably 0.1 to 20% by weight, more preferably 1% to 5% by weight.

The hair cosmetic composition according to the present invention can be prepared as, for example, hair rinses, hair conditioners, hair lotions, and hair creams, in any conventional manner.

The hair cosmetic composition according to the present invention can contain, in addition to the above-mentioned essential components (A) and (B), conventional optional ingredients, as long as the desired properties or characteristics of the present invention are not adversely affected. Examples of such optional ingredients are hydrocarbons such as liquid paraffins, vaseline, solid paraffins, squalane, and olefin oligomers; esters such as isopropyl myristate, isopropyl palmitate, stearyl stearate, octyldodecyl myristate, octyldodecyl oleate, and 2-ethylhexanoic acid triglycerides; emulsifiers such as polyoxyethylene cetyl ether, polyoxyethylene stearate, and polyoxyethylene sorbitan monolaurate; ampholytic surfactants such as disodium N-(2-hydroxyethyl)-N-bis(2-carboxyethyl)aminoethyl lauryl amide and 2-cocoyl-N-carboxymethyl-N-hydroxyethyl imidazolium betaine; anionic surfactants such as higher alcohol sulfates, alcohol ether sulfates, and α-olefin sulfonates; higher alcohols such as lauryl alcohol, cetyl alcohol, stearyl alcohol, and behenyl alcohol; higher fatty acids palmitic acid, stearic acid, and behenic acid; humectants such as ethylene glycol, propylene glycol, 1,3-butylene glycol, glycerol, and sorbitol; and solvents such as ethanol. The other optional minor components include, for example, antiseptic agents, pH adjusting agents, hair growing agents, UV absorbers, antioxidants, stabilizers, and perfumes.

According to the present invention, it is possible to obtain a hair cosmetic composition having an excellent settability, comb-through characteristic, static friction coefficient, and antistatic properties by the joint use of a specific quaternary ammonium salt shown in the above-mentioned formula (I) having an iodine value of 35 to 100 and a specific phosphate shown in formula (II).

EXAMPLES

The present invention now will be further illustrated by, but is by no means limited to, the following Examples, in which the component ratios or amounts of samples used are based on "% by weight" unless otherwise specified. The following test methods are used in the Examples.

Settability

A bundle of hair having a length of 20 cm and a weight of 1.5 g was coated with 0.2 g of the sample, thoroughly rinsed, wrapped around a rod having a diameter of 2 cm, and then dried by hot air at 50° C. for 30 minutes.

The resultant curled hair bundle was then removed from the rod and suspended in an observation chamber at a temperature of 30° C. and a relative humidity of 85% to observe uncurling of the hair. Using the length of the hair bundle immediately after placement in the observation chamber as 100% curl retention and the original length of the uncurled hair bundle, i.e., 20 cm, as 0% curl retention, the curl retention rate was calculated. The settability was evaluated by the following criteria, and the judgement was made after the hair bundle had been left for two hours in the observation chamber.

| Curl retention rate | | |
|---|---|---|
| 50% or more: | Excellent | |
| 40 to 50%: | Good | |
| 30 to 40%: | Fair | Δ |
| 20% or less: | Poor | × |

Comb-Through Characteristic

A bundle of hair having a weight of 7 g and a length of 18 cm was inserted into the teeth of a polyethylene comb and the comb lowered at a fixed speed of 40 m/min. The maximum load, i.e., resistance, applied by the bundle of hair on the comb during that time was read out from a tension meter recording needle. The rate of reduction of the maximum load for the same hair bundle before and after rinsing was used as the comb-through characteristic. The measurement conditions were a temperature of 25° C. and a relative humidity of 65%. The rinsing comprised coating 0.7 g of the sample on the hair bundle, thoroughly rinsing the bundle, then drying the bundle at 25° C. at a relative humidity of 60%.

That is, $$comb\text{-}through = (C_B - C_T)/C_B \times \phi (\%)$$

wherein $C_B$ Maximum load before rinse treatment (g)
$C_T$ Maximum load after rinse treatment (g)

The comb-through characteristic was evaluated by the following criteria:

| 50% or more: | Excellent | |
|---|---|---|
| 40 to 50%: | Good | |
| 30 to 40%: | Fair | Δ |
| 20 to 30%: | Poor | × |
| 20% or less: | Bad | ×× |

Static Friction Coefficient

A single strand of hair with 40 g weights attached to both ends thereof was placed on the pulley of a friction coefficient meter and the pulley turned at a speed of 2 rpm. The friction coefficient at that time was measured and used as the static friction coefficient.

The static friction coefficient was evaluated by the following criteria:
Less than 0.12:A
0.12 to less than 0.14:B
0.14 or more:C Note that the sample hair used was hair which had been rinsed during the evaluation of the comb-through.

Antistatic Properties

A bundle of hair having a weight of 8.5 g and a length of 20 cm was combed through 10 times at 20 second intervals using a polyester comb, placed in a Faraday box, and the amount of electricity generated in the bundle of hair by the combing was measured by a potentiometer. The antistatic property was considered to be the rate of reduction of the amount of electricity in the same hair bundle before and after rinsing by 0.9 g of the sample composition.

$$Antistatic\ property = (Q_B - Q_T)/Q_B \times 100(\%)$$

where,
$Q_B$: Amount of electricity before rinsing (coulombs)
$Q_T$ Amount of electricity after rinsing (coulombs)

The antistatic property was evaluated by the following criteria:

| 90% or more: | Excellent | ◎ |
|---|---|---|
| 70 to 90%: | Good | ○ |
| 50 to 70%: | Fair | Δ |
| 30 to 50%: | Poor | × |
| 30% or less: | Bad | ×× |

EXAMPLE 1 AND COMPARATIVE EXAMPLES 1 TO 7

Seven kinds of hair rinses having the compositions listed in Table 1 were prepared. The characteristics of the resultant hair rinses were evaluated as mentioned above.

The results are shown in Table 1.

TABLE 1

| Ingredient | Iodine Value | Comparative Example | | | | | | | Example |
| --- | --- | --- | --- | --- | --- | --- | --- | --- | --- |
| | | 1 | 2 | 3 | 4 | 5 | 6 | 7 | 1 |
| Stearyl trimethyl ammonium chloride | 0 | 1.0% | — | — | — | — | — | — | — |
| Distearyl dimethyl ammonium chloride | 28 | — | 1.0% | — | — | — | 1.0% | — | — |
| Dioleyl dimethyl ammonium chloride | 70 | — | — | 1.0% | — | — | — | — | 1.0% |
| Dibrassidyl dimethyl ammonium chloride | 60 | — | — | — | — | — | — | 1.0% | — |
| Phosphate *1 | | — | — | — | 5.0% | 5.0 | 5.0 | 5.0 | 5.0 |
| Cetostearyl alcohol | — | 3.0 | 3.0 | 3.0 | 3.0 | 3.0 | 3.0 | 3.0 | 3.0 |

TABLE 1-continued

| Ingredient | Iodine Value | Comparative Example 1 | 2 | 3 | 4 | 5 | 6 | 7 | Example 1 |
|---|---|---|---|---|---|---|---|---|---|
| Propylene glycol | — | 10.0 | 10.0 | 10.0 | 10.0 | 10.0 | 10.0 | 10.0 | 10.0 |
| Purified water | | Balance | Balance | Balance | Balance | Balance | Balance | Balance | Balance |
| Total | | 100.0% | 100.0% | 100.0% | 100.0% | 100.0% | 100.0% | 100.0% | 100.0% |
| Settability | | x | x | x | o | o | o | o | ⊚ |
| Comb-through characteristic | | Δ | Δ | Δ | xx | Δ | Δ | Δ | ⊚ |
| Static friction coefficient | | B | B | B | C | B | B | B | A |
| Antistatic Property | | Δ | Δ | Δ | xx | Δ | Δ | o | ⊚ |

$(C_4H_9\text{---}(OCH_2CH)_{\overline{21}}\text{---}O)_{\overline{x}}P(OH)_y$ wherein $x = 1$, $y = 2$ (monoester) or $x = 2$, $y = 1$ (diester)
  |
  $CH_3$    O Ratio of monoester/diester = 80/20

As is clear from the results shown in Table 1, the comparative hair rinses, in which the quaternary ammonium salt was used alone (i.e., Comparative Examples 1 to 3), the phosphate was used alone (i.e., Comparative Example 4), the quaternary ammonium salt having the iodine value not within the range of the present invention and the phosphate were used together (i.e., Comparative Examples 5 and 6), and the quaternary ammonium salt having the alkenyl group with 22 carbon atoms (i.e., Comparative Example 7), did not exhibit the desired settability, comb-through characteristic, static friction coefficient, and antistatic properties. Contrary to this, the hair rinse composition of Example 1 according to the present invention exhibited satisfactory results.

EXAMPLES 2 TO 5 AND COMPARATIVE EXAMPLE 8

The hair cosmetic compositions in the form of aqueous dispersions having the following compositions were prepared by using the synthetic dialkenyl dimethyl ammonium chloride listed in Table 2 and the following phosphate ester, as the starting materials. The quaternary ammonium salts were prepared from the natural fatty acids having various unsaturations of alkyl groups and carbon number distributions.

| Ingredient | % |
|---|---|
| Dialkenyl dimethyl ammonium chloride | 1.0 |
| Phosphate*2 | 5.0 |
| Cetostearyl alcohol | 3.0 |
| Propylene glycol | 10.0 |
| Water | Balance |

-continued

| Ingredient | % |
|---|---|
| | 100.0 |

*2 $(R\text{---}(OCH_2\text{---}CH)_{\overline{m}}\text{---}O)_{\overline{x}}P(OH)_y$
           |
         $CH_3$    O R = glyceryl, m = 90, x = 1, y = 2 (monoester) or x = 2, y = 1 (diester) monoester/diester = 70/30

TABLE 2

| No. | Name | Starting fatty acid Approximate composition (%) | | | | | | | | | | Iodine value | Settability | Comb-through characteristic | Static friction coefficient | Antistatic property |
|---|---|---|---|---|---|---|---|---|---|---|---|---|---|---|---|---|
| | | Saturated fatty acid | | | | | Unsaturated acid* | | | | | | | | | |
| | | $C_{12}$ | $C_{14}$ | $C_{15}$ | $C_{18}$ | $C_{20}$ | $C_{18}'$ | $C_{18}''$ | $C_{18}'''$ | $C_{20}'$ | $C_{22}'$ | | | | | |
| Example 2 | Palm oil fatty acid | — | 1 | 45 | 4 | — | 42 | 8 | — | — | — | 35 | | o | A | ⊚ |
| Example 3 | Soybean oil fatty acid | — | — | 12 | 4 | — | 25 | 51 | 8 | — | — | 82 | o | ⊚ | A | ⊚ |
| Example 4 | Tall oil fatty acid | — | — | ← | 10 | → | 45 | 45 | — | — | — | 86 | ⊚ | ⊚ | A | ⊚ |
| Example 5 | Safflower oil fatty acid | — | — | 6 | 2 | — | 80 | 12 | — | — | — | 92 | ⊚ | o | A | ⊚ |
| Comparative Example 8 | Linseed oil fatty acid | — | — | 6 | 4 | — | 22 | 15 | 52 | — | — | 115 | ⊚ | x | C | ⊚ |

*' represents the number of the double bond.

As is clear from the results shown in Table 2, when the hair cosmetic compositions were formulated from the quaternary ammonium salts obtained by using, as starting materials, the fatty acids having 14 to 18 carbon atoms, the desired excellent results were obtained if the iodine value of the quaternary ammonium as well as the carbon atom number of each of the four hydrocarbon groups attached to the nitrogen atom satisfy the scope of the present invention. But even if the carbon atom numbers of the four hydrocarbon groups were within the scope of the present invention, the desired result could be obtained if the iodine value of the quaternary ammonium was out of the scope of the present invention.

EXAMPLE 6

The following hair treatment composition was prepared and was evaluated in the same manner as mentioned above.

| Ingredient | % |
|---|---|
| Dioleyl dimethyl ammonium chloride (iodine value = 40) | 2.0 |
| Phosphate*3 | 6.0 |
| Cetostearyl alcohol | 5.0 |
| Liquid paraffin | 3.0 |
| P.O.E. Stearyl ether | 1.0 |

-continued

| Ingredient | % |
| --- | --- |
| Propylene glycol | 10.0 |
| Perfume | 0.5 |
| Coloring agent | trace |
| Purified water | balance |
| | 100.0 |

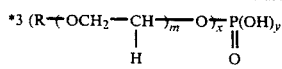

wherein

R: $C_{16}/C_{18}=7/3$, m=3, x=1, y=2 (monoester) or x=2, y=1 (diester), Monoester/Diester=90/10

The results are as follows:

| | |
| --- | --- |
| Settability: | O |
| Comb-through characteristics: | ⊚ |
| Statistic friction coefficient: | A |
| Antistatic properties: | O |

EXAMPLE 7

The following hair treatment composition was prepared and was evaluated in the same manner as mentioned above.

| Ingredient | % |
| --- | --- |
| Dioleyl dimethyl ammonium chloride | 2.0 |
| Phosphate*4 | 6.0 |
| Cetostearyl alcohol | 5.0 |
| Liquid paraffin | 3.0 |
| P.O.E. Stearyl ether | 1.0 |
| Propylene glycol | 10.0 |
| Perfume | 0.5 |
| Coloring agent | trace |
| Purified water | balance |
| | 100.0 |

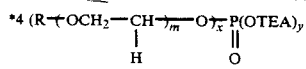

wherein

R: $C_{16}/C_{18}=7/3$, m=3, x=1, y=2 (monoester) or x=2, y=1 (diester),

Monoester/Diester=90/10

TEA=Triethanolamine

The results are as follows:

| | |
| --- | --- |
| Settability: | O |
| Comb-through characteristics: | O |
| Statistic friction coefficient: | A |
| Antistatic properties: | O |

We claim:

1. A hair cosmetic composition comprising:

(A) at least one quaternary ammonium salt in an amount of 0.05 to 10% by weight, having the formula:

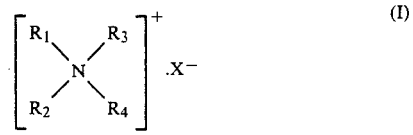

wherein $R_1$ is an alkenyl having 14 to 24 carbon atoms, $R_2$ in an alkyl or alkenyl having 14 to 24 carbon atoms, $R_3$ and $R_4$ are independently methyl, ethyl, a polyoxyethylene having an average polymerization degree of 1 to 5, or polyoxypropylene having an average polymerization degree of 1 to 5, and $X^-$ is an anion, and having an iodine value of 35 to 100; and (B) a phosphate in an amount of 0.05 to 10% by weight, having the formula:

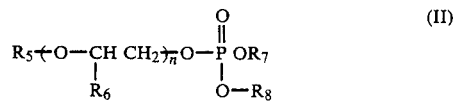

wherein $R_5$ is a linear alkyl having 1 to 22 carbon atoms, a hydroxyalkyl having 1 to 22 carbon atoms, an alkenyl having 2 to 22 carbon atoms, an alkylphenyl having 7 to 22 carbon atoms, or glyceryl, $R_6$ is hydrogen or methyl, $R_7$ is hydrogen, an alkali metal, a $C_1$-$C_{20}$ alkyl-substituted ammonium, or a $C_1$-$C_{20}$ hydroxyalkyl-substituted ammonium, $R_8$ is a group having the formula:

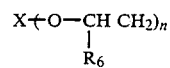

or $R_7$, n is an integer of 0 to 100, and X is the same as defined above.

2. A hair cosmetic composition as claimed in claim 1, wherein the component (A) is formulated in an amount of 0.5% to 2.5% by weight based on the weight of the composition.

3. A hair cosmetic composition as claimed in claim 1, wherein the component (B) is formulated in an amount of 0.5% to 2.5% by weight based on the weight of the composition.

4. A hair cosmetic composition as claimed in claim 1, wherein the weight ratio of the quaternary ammonium (A) to the phosphate (B) in the composition is 1/10 to 10/1.

5. A hair cosmetic composition as claimed in claim 1, wherein the total amount of the quaternary ammonium (A) and the phosphate (B) in the composition is 0.1% to 20% by weight.

* * * * *